United States Patent
Mertelmeier et al.

(10) Patent No.: US 7,729,756 B2
(45) Date of Patent: Jun. 1, 2010

(54) MEASUREMENT SYSTEM FOR EXAMINING A SECTION OF TISSUE ON A PATIENT AND THE USE OF A MEASUREMENT SYSTEM OF THIS TYPE

(75) Inventors: Thomas Mertelmeier, Erlangen (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 1362 days.

(21) Appl. No.: 10/181,402

(22) PCT Filed: Jan. 18, 2001

(86) PCT No.: PCT/DE01/00213

§ 371 (c)(1),
(2), (4) Date: Jul. 17, 2002

(87) PCT Pub. No.: WO01/52733

PCT Pub. Date: Jul. 26, 2001

(65) Prior Publication Data

US 2003/0023185 A1 Jan. 30, 2003

(30) Foreign Application Priority Data

Jan. 18, 2000 (DE) ................................. 100 01 825

(51) Int. Cl.
*A61B 5/05* (2006.01)
(52) U.S. Cl. ........................ 600/547; 600/504; 600/505; 600/506; 600/508; 600/536; 600/549; 600/373; 600/374; 324/692

(58) Field of Classification Search ................. 600/547, 600/549, 504–506, 508, 536, 437, 407, 409, 600/372, 484, 345, 374, 554, 393; 324/600, 324/603, 605, 609, 629; 607/62, 148
See application file for complete search history.

(56) References Cited

U.S. PATENT DOCUMENTS 3,566,233 A * 2/1971 Kahn et al. ................. 600/547

(Continued)

FOREIGN PATENT DOCUMENTS

DE 41 37 303 A1 5/1993

(Continued)

OTHER PUBLICATIONS

Prospekt, "TransScan TS2000" (interne Nr. BKW 62014 WS 10994), The Sooner, the Better Innovation in Breast Cancer.

(Continued)

*Primary Examiner*—Brian Casler
*Assistant Examiner*—Baisakhi Roy
(74) *Attorney, Agent, or Firm*—Young & Thompson

(57) ABSTRACT

A measurement system for examining a section of tissue on a patient in which electric current and/or voltages are applied to a patient in at least one location and are measured on the section of tissue to be examined by at least one electrode of a contact surface of the measurement system. As a result, conclusions can be drawn about the interior of the section of tissue to be examined. The electrode is at least partially surrounded by a conductor element for contacting with a potential which deviates from that of the conductor element.

24 Claims, 4 Drawing Sheets

U.S. PATENT DOCUMENTS

Figure 1:
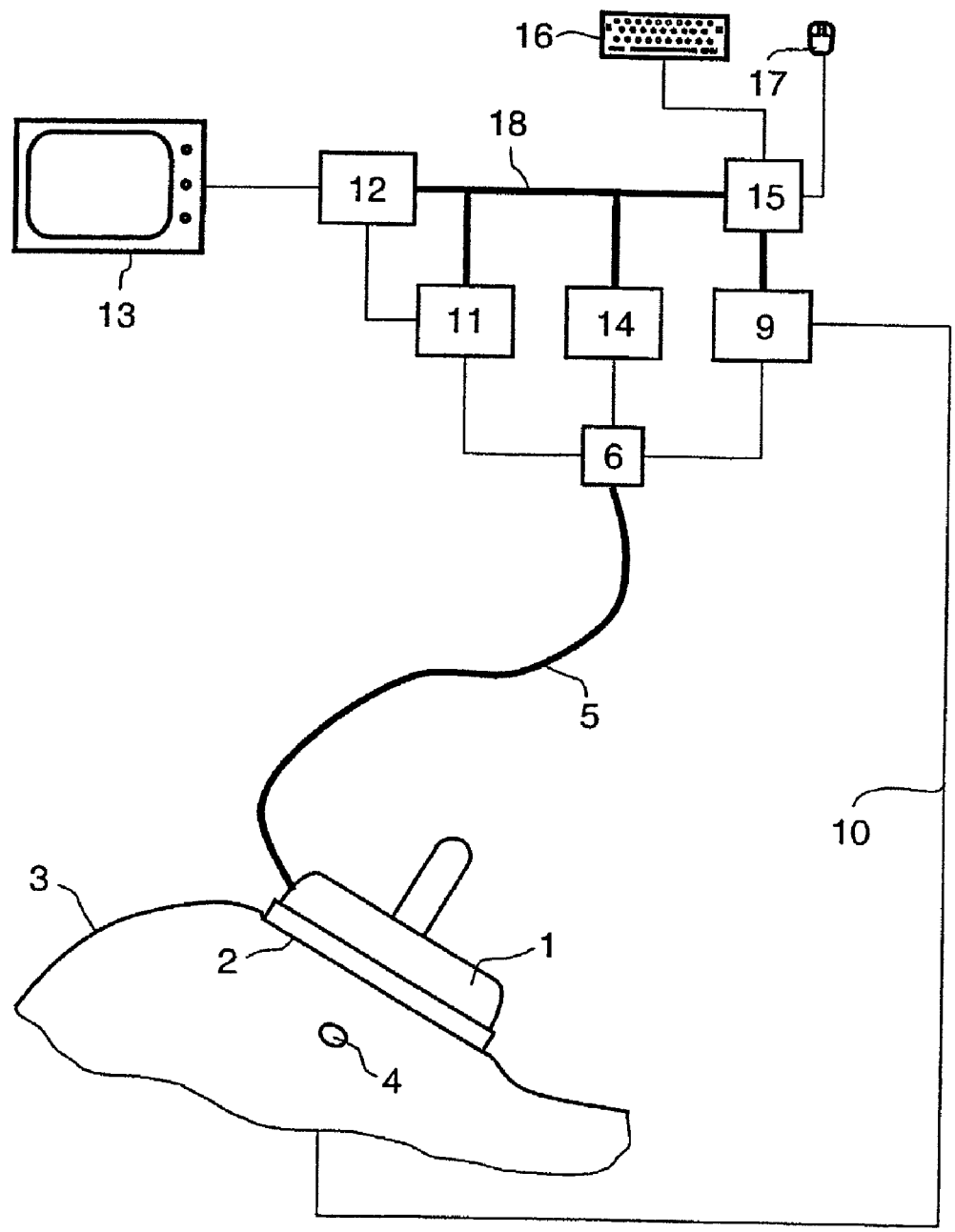

| | | | | |
|---|---|---|---|---|
| 3,784,908 A | * | 1/1974 | Anderson | 600/547 |
| 4,088,125 A | * | 5/1978 | Forgione et al. | 600/547 |
| 4,291,708 A | | 9/1981 | Frei et al. | |
| 4,407,300 A | * | 10/1983 | Davis | 600/547 |
| 4,458,694 A | * | 7/1984 | Sollish et al. | 600/547 |
| 4,486,835 A | * | 12/1984 | Bai et al. | 600/547 |
| 4,537,203 A | * | 8/1985 | Machida | 600/547 |
| 4,852,580 A | * | 8/1989 | Wood | 600/506 |
| 4,955,383 A | * | 9/1990 | Faupel | 600/407 |
| 4,969,468 A | * | 11/1990 | Byers et al. | 600/373 |
| 5,092,339 A | * | 3/1992 | Geddes et al. | 600/505 |
| 5,099,844 A | * | 3/1992 | Faupel | 600/372 |
| 5,143,079 A | | 9/1992 | Frei et al. | |
| 5,353,802 A | * | 10/1994 | Ollmar | 600/547 |
| 5,366,496 A | * | 11/1994 | Dahl et al. | 607/132 |
| 5,427,098 A | * | 6/1995 | Faupel et al. | 600/407 |
| 5,499,631 A | * | 3/1996 | Weiland | 600/547 |
| 5,560,358 A | * | 10/1996 | Arnold et al. | 600/373 |
| 5,800,350 A | * | 9/1998 | Coppleson et al. | 600/372 |
| 5,846,196 A | * | 12/1998 | Siekmeyer et al. | 600/374 |
| 6,073,039 A | * | 6/2000 | Berson | 600/372 |
| 6,091,981 A | * | 7/2000 | Cundari et al. | 600/407 |
| 6,122,544 A | * | 9/2000 | Organ | 600/547 |
| 6,157,697 A | | 12/2000 | Mertelmeier et al. | |
| 6,167,300 A | * | 12/2000 | Cherepenin et al. | 600/547 |
| 6,501,984 B1 | * | 12/2002 | Church et al. | 600/547 |
| 6,593,130 B1 | * | 7/2003 | Sen et al. | 435/285.2 |
| 6,807,444 B2 | * | 10/2004 | Tu et al. | 600/547 |
| 6,845,264 B1 | * | 1/2005 | Skladnev et al. | 600/547 |

FOREIGN PATENT DOCUMENTS

| EP | 0 945 103 A1 | 9/1999 |
|---|---|---|
| WO | WO96/12439 | 5/1996 |

OTHER PUBLICATIONS

Piperno et al., "Breast Cancer Screening by Impendence Measurements", Frontiers of Medical and Biological Engineering, NL, VSP, vol. 2, No. 2, 1990, pp. 111-117.

* cited by examiner

MEASUREMENT SYSTEM FOR EXAMINING A SECTION OF TISSUE ON A PATIENT AND THE USE OF A MEASUREMENT SYSTEM OF THIS TYPE

This application of a 371 of PCT/DE01/00213 filed on Jan. 18, 2001.

FIELD OF THE INVENTION

The invention relates to a measuring arrangement for examining a tissue section of a patient, having an electrode array, a signal source, a measuring circuit and potential means, the signal source subjecting the patient via at least one electrode of the electrode array to electrical currents and/or voltages, which the measuring circuit measures on at least one electrode of the electrode array, and the electrode array being surrounded at least partially by an electrical conductor element, to which the potential means apply a potential that differs from the potential of the electrodes of the electrode array. The invention furthermore relates to a use of such a measuring arrangement.

BACKGROUND OF THE INVENTION

From the prior art, for example from the SIEMENS brochure "TransScan TS 2000" (internal No BKW 62014 WS 10994), measuring arrangements for examining tissue sections of a patient are known, in which the electrode array is surrounded by an electrical conductor element in the form of a metal strip ("guard ring"), the metal strip and the electrodes of the electrode array being operated with an identical potential. Although this improves the detectability of conductivity inhomogeneities of the tissue section to be examined, undesired signal intensifications occur at the image edges of the impedance image.

SUMMARY OF THE INVENTION

It is an object of the invention to design a measuring arrangement of the type mentioned in the start in such a way that such undesired edge effects are avoided as far as possible or completely. It is also an object to provide a use of such a measuring arrangement.

In the measuring arrangement, the conductor element surrounding the electrode array is hence at a potential which differs from the potential of the electrodes of the electrode array, and which is preferably below the potential of the electrodes of the electrode array.

In particular when the conductor element has a lower potential than the electrodes, the undesired edge effects in the impedance images are at least moderated and often fully eliminated. Since the intensified signal values at the image edges of the impedance images are thereby at least reduced, an improved image quality of the impedance images is obtained, that is to say conductivity inhomogeneities, for example due to carcinomas or tumors that are present, can be recognized or detected better.

The conductor element may be a metal element, or a plastic element made of a conductive plastic material, which can be adapted in terms of its geometry, in particular its width, to the respective application of the measuring arrangement, for example to breasts of differing size in the case of mammary diagnosis.

In an advantageous embodiment of the measuring arrangement, a further improvement in the image quality is achieved by adding at least one further conductor element, which advantageously likewise has a potential that differs from the potential of the electrodes of the electrode array; according to a variant of the invention, different potentials are respectively applied to the individual conductor elements, so that a desired potential profile can be achieved over the total width of all the active conductor elements. During the examination, the potential and the number of conductor elements that are used can be selected individually as a function of the type, size and shape of the tissue section to be examined, in order to achieve sufficient suppression of undesired edge effects.

According to a further particularly advantageous embodiment, the electrodes of the measuring arrangement are surrounded by an inner conductor element and an outer conductor element. In this case, the electrodes are operated with the potential 0 mV, the inner conductor element is operated in a potential range of below from 0 mV to −5 mV, and the outer conductor element is operated with a potential of −15 mV. In this case, the potential of the conductor element is adjusted, as a function of the respective potential of the outer conductor element, either automatically or by an operator, in such a way that there is sufficient suppression of the undesired edge effects of the impedance images.

When a plurality of conductor elements are provided, the respective potential allocation and/or the activation of a particular number of conductor elements, or the activation of particular conductor elements, may be carried out with the aid of particular presettings that have been found from experience to be favorable for the specific tissue section to be examined. Such presettings may initially be carried out automatically and then modified by an operator and adapted to the actual tissue section, in order to achieve a particularly high image quality.

If a plurality of conductor elements are provided, these may be designed with differing geometries, and they may in particular have a differing width.

The conductor element, or the conductor elements, may surround the electrode array partially or fully. It is also possible to provide local conductor elements which, for example, are arranged in the corner regions of the electrode array in order to counteract undesired edge effects that occur more strongly there.

In this case, according to a variant of the invention, the local conductor elements have a potential applied to them which differs from the potential of a conductor element and the potential of the electrodes. With respect to the local conductor elements as well, the respective potential allocation and/or the activation of a particular number of local conductor elements, or the activation of particular local conductor elements, may be carried out with the aid of particular presettings that have been found from experience to be favorable for the respective tissue section to be examined; a presetting initially carried out automatically may be followed by individual adaptation by an operator.

According to a further advantageous embodiment, at least one conductor element may be made of a material with limited conductivity (a resistor material, e.g. a resistor alloy that is known per se, such as chromium-nickel, constantan, etc.) in order to form a potential gradient. This gives rise, for example, to potential profiles that decrease or increase over the width of the conductor element, or other desired potential profiles, by applying different potentials to the conductor element at its edges.

The use according to the invention of the measuring arrangement consists in finding tumors in living human tissue, in particular in mammary diagnosis to find tumors in living human breast tissue.

BRIEF DESCRIPTION OF THE INVENTION

Figure 2:
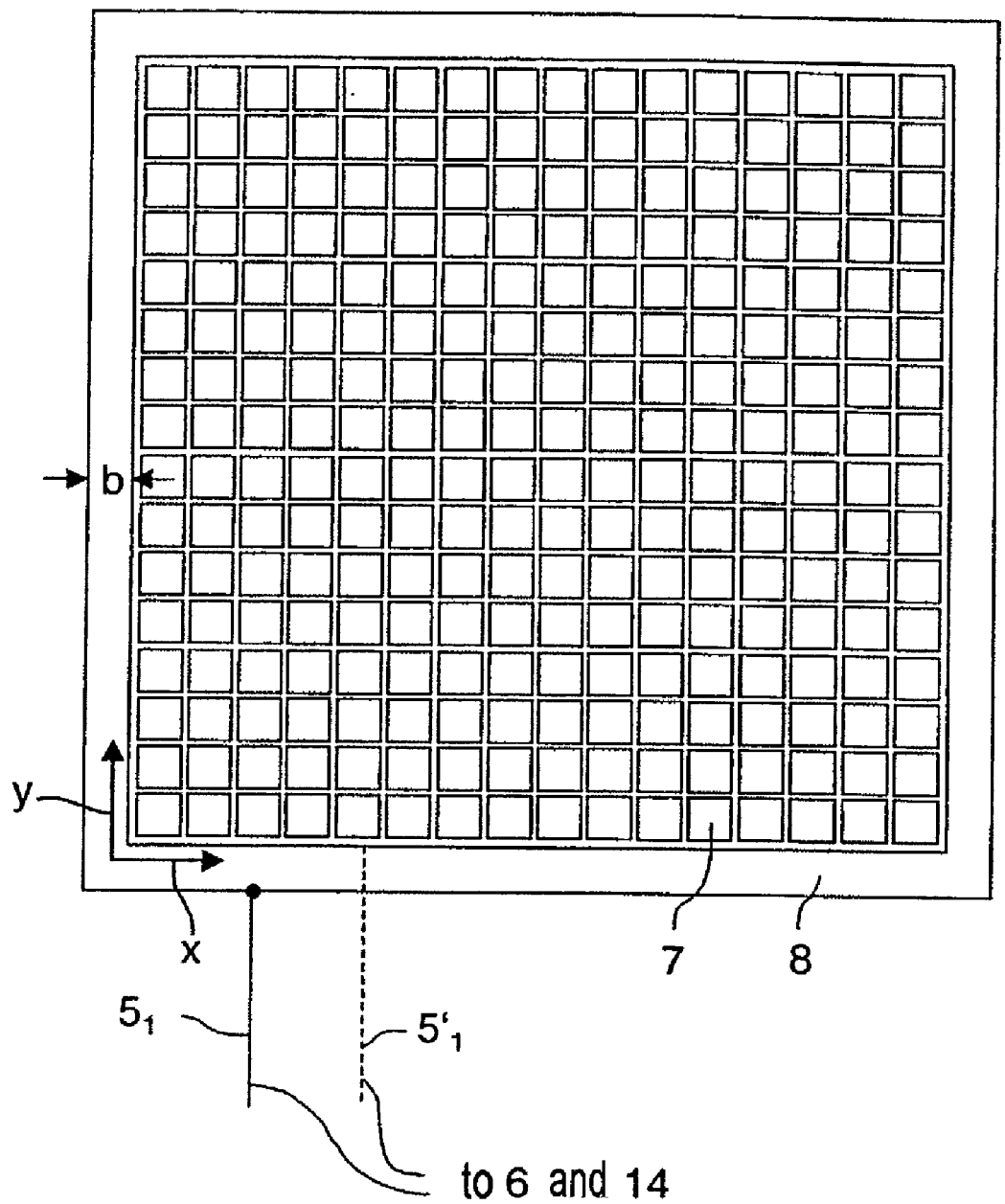
Figure 3:
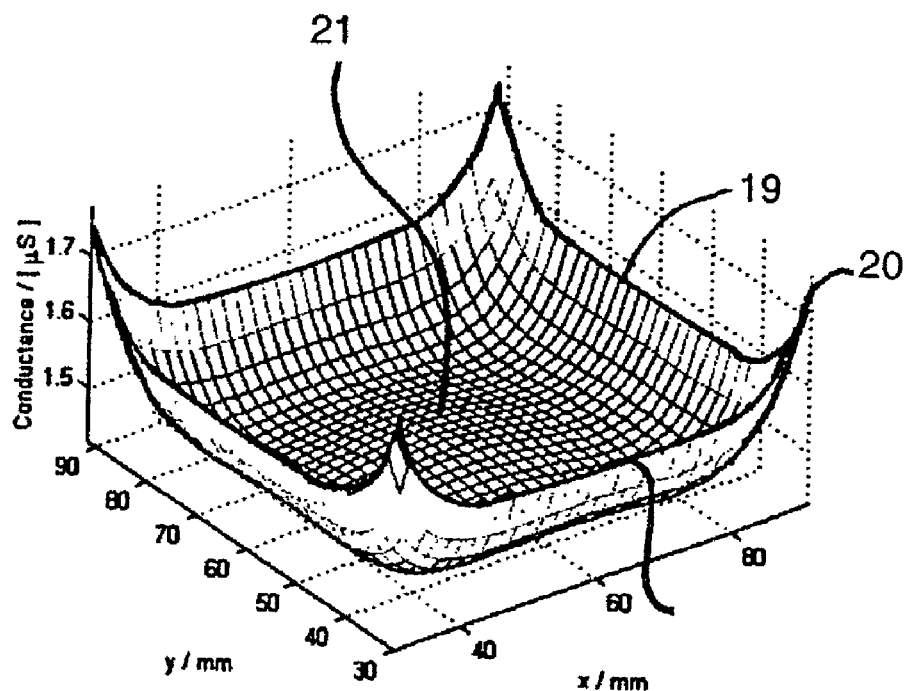
Figure 4:
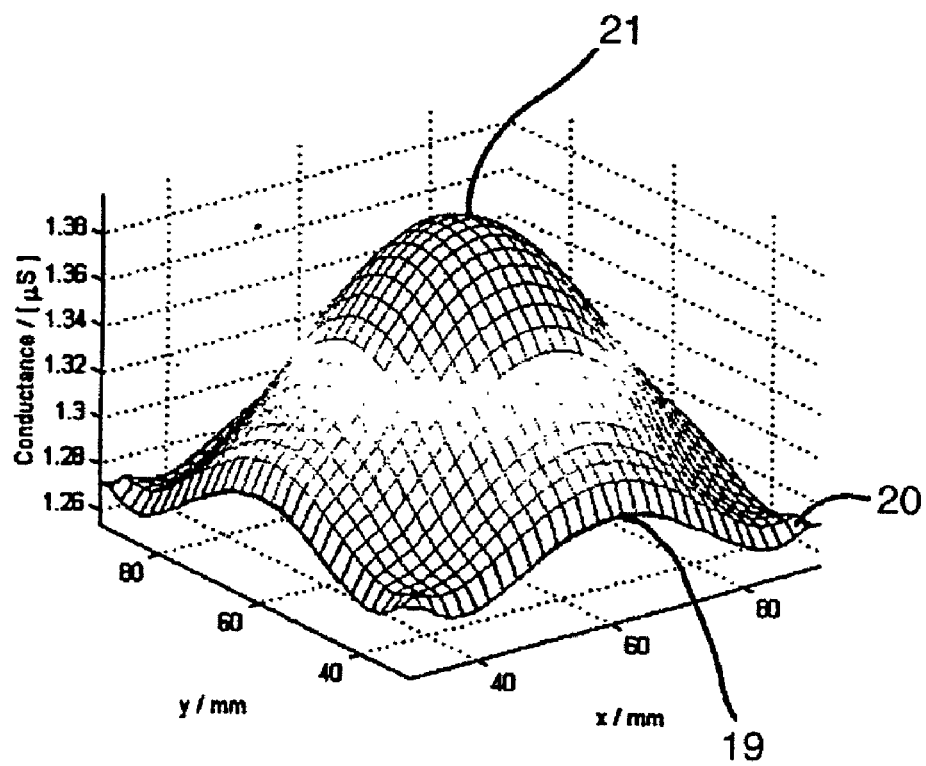
Figure 5:
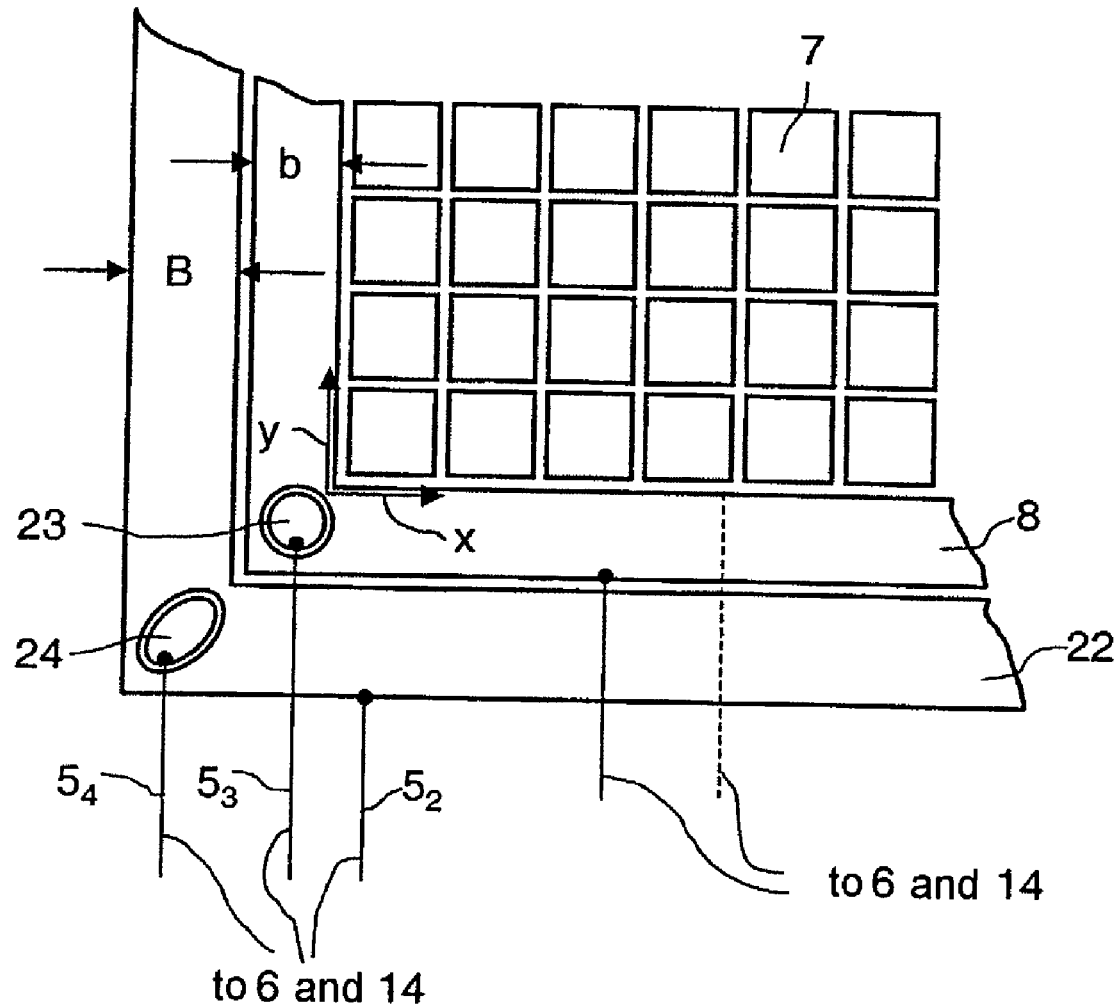

Further details of the invention can be found in exemplary embodiments of the invention that are explained below and are represented in the drawings, in which:

FIG. 1 shows a measuring arrangement according to the invention in a roughly schematic, partially block-diagrammatic representation, FIG. 2 shows the electrode arrangement of the device according to FIG. 1, FIG. 3 shows an impedance image which is recorded with a measuring arrangement according to the prior art, FIG. 4 shows an impedance image recorded with the measuring arrangement according to the invention, FIG. 5 shows, in a similar representation to FIG. 2, a detail of the electrode arrangement of a variant of the measuring arrangement according to the invention.

DETAILED DESCRIPTION OF THE INVENTION

FIG. 1 shows a measuring arrangement according to the invention which, in the case of the application that is represented, is used to find a tumor in living human tissue, an application from mammary diagnosis being illustrated, which involves recognizing tumors in living human breast tissue.

The measuring arrangement and has a hand-held applicator 1 whose application face 2 is brought, by the operator, into contact with the surface of that tissue section, that is to say of a mamma 3, in which a tumor 4 is suspected.

On its application face 2, the applicator 1 has an electrode arrangement, yet to be described, whose electrodes and conductor elements are connected to an interface circuit 6 via a multistranded cable 5.

The electrode arrangement is represented in FIG. 2 and, in the case of the exemplary embodiment that is described, it has an electrode array with square electrodes, referred to hereafter as individual electrodes 7, that are arranged in a matrix and are electrically insulated from one another, which array is fully surrounded by a frame-like conductor element 8, the conductor element 8 being electrically insulated from the individual electrodes 7.

In order to carry out a measurement, electrical voltages and/or electrical currents are delivered by means of a signal source 9, via the interface 6 and the cable 5, to one or, simultaneously or successively, a plurality of individual electrodes 7, depending on the operating mode. Since the patient is placed at a reference potential, for example −2.5 V, by means of a reference electrode (not shown), which is for example hand-held, via a line 10 connected to the signal source 9, the tissue section, which is to be examined, of the mamma 3 is subjected to electrical currents and/or voltages.

These currents and/or voltages are measured by means of a measuring circuit 11. To that end, the respective active corresponding individual electrode(s) 7, which is (are) at earth potential, is (are) connected to the measuring circuit 11 via the cable 5 and the interface unit 6. From the measured electrical currents and/or voltages, an evaluation unit 12 calculates an impedance image which is displayed on a monitor 13.

Potential means 14 are furthermore provided, which are connected to the conductor element 8 via the interface unit 6 and the cable 5, and which are used to place the conductor element 8 at a potential that differs from that of the individual electrodes 7, and is preferably less than the potential of the individual electrodes 7.

A control unit 15, to which a keyboard 16 and a further operating element are connected, the latter being a mouse 17 in the case of the exemplary embodiment that is described, is used to control the measuring arrangement and is to that end connected, via a control bus 18, to the signal source 9, the measuring circuit 11, the evaluation circuit 12 and the potential means 14. The measuring arrangement is operated by means of the keyboard 16 and the mouse 17, for example with the aid of user menus which are displayed on the monitor 13.

As explained in the introduction, in the case of the prior art the conductor element 8 is at the same potential as the individual electrodes 7. An impedance image produced for this operating state is represented in FIG. 3 and has intensified signals at its edges 19 and corners 20, which correspond to the edges and corners of the electrode arrangement, while at the center 21 of the impedance image, even though the tumor 4 to be detected is situated there, there is a weak signal that is recognizable only with difficultly.

Since, during a measurement in the case of the measuring arrangement according to the invention, the conductor element 8 is connected via the line $5_1$ and the interface unit 6 of the cable 5 to the potential means 14, and it is placed at a potential below the potential of the individual electrodes 7, for example at a potential of −0.5 mV, the intensified signals at the edges 19 and the corners 20 of the impedance images are suppressed, so that the actual signal to be detected is very pronounced at the center 21 of the impedance image and the tumor 4 can therefore be clearly found.

When the conductor element is made of a material with limited conductivity, that is to say a resistor material, and hence forms a flat ohmic impedance, it is possible to achieve a potential that varies over the width b of the conductor element 8 (voltage or potential gradient) if, during a measurement, the outer edge of the conductor element 8 is connected to the potential means 15 via the line $5_1$ and the interface unit 6, and the inner edge of the conductor element 8, as indicated by dashes, is connected to the potential means 15 via the line $5'_1$ and the interface unit 6, and if they are placed at differing potentials by the potential means 15, for example 0 mV on the inner edge and ±5 mV on the outer edge, so that a voltage profile is set up, for example decreasing linearly over the width b of the conductor element 8, by means of which particularly effective suppression of undesired edge effects in the impedance image, and therefore a further improved image quality in the vicinity of the edges 19 of the impedance image, are achieved.

An even more improved image quality in the vicinity of the edges 19 of the impedance image can be achieved, according to FIG. 5, when the electrode arrangement that is in other regards constructed according to FIG. 2 has a second frame-like conductor element 22, which fully surrounds the conductor element 8, is electrically insulated from the conductor element 8 and the individual electrodes 7, and is connected to the potential means 14 via a line $5_2$ and the interface unit 6. During a measurement, the potential means 14 place the inner conductor element 8 at, for example a potential of −5 mV, and the outer conductor element 22 at a potential of −15 mV, while the individual electrodes 7 are aat a potential of 0 mV.

When the inner conductor element 8, as described above in conjunction with the conductor element 22, is made of resistor material, the opportunity exists, in the manner already described, to place the inner edge of the conductor element 8 at a potential of 0 mV and the outer edge at a potential of −5 mV.

The outer conductor element 22, having a larger width B than the inner element 8, may also be made of resistor material (this is not shown). In this case, the potential means 14 apply a potential of −5 mV or slightly higher to the inner edge of the conductor element 22, and a potential of −15 mV to the outer edge of the outer conductor element 22. As in the case of the inner conductor element 8, this results in a potential gradient over the width B of the conductor element 22, which has an improving effect on the image quality.

In order to further improve the image quality in the vicinity of the corners 20 of the impedance images, in the case of FIG. 5 local conductor elements 23 and 24 are provided in the vicinity of the corners of the conductor elements 8 and 22. They are electrically insulated from one another and from the conductor elements 8 and 22, as well as from the individual electrodes 7, and they are connected via lines $5_3$ and $5_4$ and the interface unit 6 to the potential means 14. The latter place the local conductor elements 23 and 24 at potentials which lie below the potential of the corresponding conductor element 8 or 22, respectively. For example, the potential means 14 place the local conductor element 23 at a potential of −7 mV and the local conductor element 24 at a potential of −20 mV.

By means of this, signal intensifications possibly still existing in spite of the conductor elements 8 and 22 are broken down in the vicinity of the corners 20 of the impedance images.

The electrode arrangement may have more than two conductor elements, which surround the electrode array, which have differing widths and to which the potential means 14 apply differing potentials.

These further conductor elements may also be made of material with limited conductivity, so that potential profiles decreasing or increasing over their width, or other desired potential profiles, can be implemented.

In the case of FIG. 5, local conductor elements are provided in the vicinity of all the conductor elements. This need not necessarily be the case. Instead, the presence of local elements may be limited to some of the conductor elements. Furthermore, as in the case of FIG. 2, local conductor elements may be omitted entirely.

In the case of the exemplary embodiment according to FIG. 5, the local conductor elements are provided in the vicinity of the corners of the conductor elements surrounding the electrode array. The local conductor elements, however, may also be arranged at other points. It is also possible to provide local conductor elements in the vicinity of the corners of the conductor elements surrounding the electrode array and, in addition to them, further local conductor elements.

In the case of the exemplary embodiments that are described, the conductor elements 8 and 22 fully surround the matricial arrangement of the individual electrodes 7 of the electrode array. Provision may also be made, however, for the conductor elements to surround the electrode array only partially.

The number of conductor elements fully or partially surrounding the electrode array, as well as the number of local conductor elements, are to be taken only as examples in the case of the exemplary embodiments that are described.

The square geometry of the electrode array shown in the case of the exemplary embodiments, and likewise the square configuration of the individual electrodes, the frame-like configuration of the conductor elements surrounding the electrode array, as well as the circular or elliptical configuration of the local conductor elements, are to be taken only as examples. Differing arrangements and geometries are also possible as a function of the respective application of the measuring arrangement.

The conductor elements fully or partially surrounding the electrode array, as well as the local conductor elements, need not all be active, that is to say placed at a potential that differs from the potential of the individual electrodes. Further, not all the active conductor elements need to be placed at a potential below the potential of the individual electrodes; instead, it may also be advantageous to place individual conductor elements at a potential that is positive in relation to the individual electrodes.

In the case of the exemplary embodiment that is described, the impedance images are three-dimensional representations of the measured conductance in microsiemens (µS). In this case, x and y axes run parallel to the bounding edges of the electrode array, for which reason x and y axes are also indicated in FIG. 2 and FIG. 5. The conductance is plotted on the z axis.

Alternatively, the respectively measured conductance may also be converted into a gray value according to a conductance/gray-value scale, and a two-dimensional black-and-white impedance image may thereby be produced and displayed.

Provision may be made for the control unit 15 to produce a test image initially, before the actual measurement is carried out, for it to evaluate this test image with respect to the signal values at the edges and corners and, on the basis of this evaluation, for it to drive the potential means 14 in such a way that suitable potentials are applied to the conductor element, or to the conductor elements. In this case, the automatic selection of the conductor elements to be activated, as well as the automatic adjustment of the potentials, are carried out while taking into account the type and size of the tissue section to be determined, these data being entered, for example, by means of the keyboard 16.

Alternatively, the measuring arrangement may be operated in such a way that a test image is initially produced and, on the basis of this test image, an operator uses the keyboard 16 or the mouse 17 to adjust the potentials of the conductor element, or of the conductor elements, whereupon a further image is produced. So long as suitable potentials have been selected by the operator, this image will then be the desired impedance image. Otherwise, the potentials will be varied in the scope of an iterative process, until an impedance image of sufficient quality is obtained.

Provision may furthermore be made for automatically performed adjustments to be modified manually by an operator with a view to optimum adaptation to the respective examination case.

The exemplary embodiments that are described relate to mammary diagnosis. The measuring arrangement according to the invention, however, is also suitable for other applications, and in particular for the examination of non-female patients.

The invention claimed is:

1. A measuring arrangement for examining a tissue section of a patient, comprising:
    an electrode array in a plane and arranged to directly contact a surface of a tissue section of a patient;
    a signal source;
    a measuring circuit;
    potential means;
    the signal source subjecting the tissue section via direct contact by at least one electrode of the electrode array to electrical currents and/or voltages, which the measuring circuit measures on at least one electrode of the electrode array; and
    an electrical conductor element that is coplanar with said electrode array, said electrical conductor element being attached to and surrounding a periphery of said electrode array, said potential means applying a potential to said electrical conductor element that differs from the potential of the electrodes of the electrode array.

2. The measuring arrangement as claimed in claim 1, in which a potential that is less than the potential of the electrodes is applied to the conductor element by the potential means.

3. The measuring arrangement as claimed in claim 1, in which the conductor element (2) is designed as a metal element.

4. The measuring arrangement as claimed in claim 1, in which the conductor element (2) is designed as a plastic element.

5. The measuring arrangement as claimed in claim 1, in which at least one further conductor element (2) is provided.

6. The measuring arrangement as claimed in claim 5, in which the potential means apply different potentials to the individual conductor elements (2).

7. The measuring arrangement as claimed in claim 6, in which the electrode on which the measuring circuit measures is at a potential of 0 mV, and the potential means apply a potential that is less than 0 mV and not below −5 mV to an inner conductor element, and they apply a potential of −15 mV to an outer conductor element.

8. The measuring arrangement as claimed in claim 6, in which the potential means adjust the potentials of the individual conductor elements as a function of the type and size of the tissue section to be examined.

9. The measuring arrangement as claimed in claim 5, in which the conductor elements (2) are designed with differing geometries.

10. The measuring arrangement as claimed in claim 9, in which the conductor elements (2) have a differing width (3).

11. The measuring arrangement as claimed in claim 9, whose electrode array has at least one local conductor element (4).

12. The measuring arrangement as claimed in claim 11, in which the local conductor element (4) is arranged in a corner region (5) of the electrode array.

13. The measuring arrangement as claimed in claim 11, in which a potential that differs from the potential of a conductor element and from the potential of the electrodes is applied to a local conductor element by the potential means.

14. The measuring arrangement as claimed in claim 11, in which the potential means adjust the potentials of the individual local conductor elements as a function of the type and size of the tissue section to be examined.

15. The measuring arrangement as claimed in claim 1, in which at least one conductor element (2) is made of a material with limited conductivity in order to form locally differing potentials.

16. The measuring arrangement as claimed in claim 15, in which a conductor element (2) is formed from a material with limited conductivity as a flat ohmic impedance.

17. The measuring arrangement as claimed in claim 15, in which a conductor element (2) made of a material with limited conductivity has edges (9 and 10), on which the potential means apply differing potentials to it.

18. The measuring arrangement as claimed in claim 1, wherein the electrode array and the electrical conductor element are arranged and adapted to directly contact a same tissue section of the patient.

19. A measuring arrangement for examining a tissue section of a patient, comprising:
a matrix of m by n plural first electrodes in a plane and that are electrically insulated from each other, each of m and n being greater than one;
a second electrode that is coplanar with said matrix and completely surrounding and directly attached to said matrix around an entire periphery of said matrix and being electrically insulated from said first electrodes, said first electrodes and said second electrode being arranged and adapted to directly contact a same surface of a same tissue section of a patient;
a signal source connected to said first electrodes and that applies an electrical signal through direct contact by at least one of said first electrodes to the patient;
a measuring circuit that is connected to said first electrodes and measures the electrical signal thereon; and
a source of an electrical potential that is less than an electrical potential of said first electrodes, said source being connected to said second electrode.

20. The arrangement of claim 19, further comprising a further source of electrical potential that is less than the electrical potential of said second electrode, and a third electrode at least partially surrounding said second electrode and electrically insulated from said first and second electrodes, said third electrode being connected to said further source.

21. The arrangement of claim 19, further comprising a further source of electrical potential that is less than the electrical potential of said second electrode, and a local conductor element at a corner of said second electrode and electrically insulated from said first and second electrodes, said local conductor element being connected to said further source.

22. The arrangement of claim 19, further comprising a further source of electrical potential that is less than the electrical potential of said second electrode, and wherein said source is connected to an inner edge of said second electrode and said further source is connected to an outer edge of said second electrode.

23. The arrangement of claim 19, wherein the plane is flat.

24. A measuring arrangement for examining a tissue section of a patient, comprising:
an electrode array that is arranged to directly contact a surface of a tissue section of a patient;
a signal source;
a measuring circuit;
potential means; and
an electrical conductor element that is directly attached to and surrounds a periphery of said electrode array and that is electrically insulated from said electrode array, said potential means applying a potential to said electrical conductor element that differs from the potential of the electrodes of the electrode array, said electrical conductor element being arranged to directly contact the same surface of the same tissue section directly contacted by said electrode array,
wherein the signal source subjects the tissue section via direct contact by at least one electrode of the electrode array to electrical currents and/or voltages that the measuring circuit measures on at least one electrode of the electrode array.

* * * * *